(12) United States Patent
Cronin et al.

(10) Patent No.: US 11,167,083 B2
(45) Date of Patent: Nov. 9, 2021

(54) SYSTEM AND METHOD FOR MONITORING PATIENT IN A MAGNETIC RESONANCE IMAGING ENVIRONMENT

(71) Applicant: KONINKLIJKE PHILIPS N.V., Eindhoven (NL)

(72) Inventors: John Cronin, Bonita Springs, FL (US); Michael D'Andrea, Bonita Springs, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 713 days.

(21) Appl. No.: 16/062,829

(22) PCT Filed: Dec. 30, 2016

(86) PCT No.: PCT/EP2016/082943
§ 371 (c)(1),
(2) Date: Jun. 15, 2018

(87) PCT Pub. No.: WO2017/114960
PCT Pub. Date: Jul. 6, 2017

(65) Prior Publication Data
US 2020/0261647 A1     Aug. 20, 2020

Related U.S. Application Data

(60) Provisional application No. 62/274,057, filed on Dec. 31, 2015.

(51) Int. Cl.
*A61B 5/055* (2006.01)
*A61M 5/142* (2006.01)
(Continued)

(52) U.S. Cl.
CPC .......... *A61M 5/172* (2013.01); *G05B 19/042* (2013.01); *G16H 40/20* (2018.01); *G16H 40/67* (2018.01);
(Continued)

(58) Field of Classification Search
CPC ... A61B 5/415; A61B 5/055; A61B 2090/374; A61B 6/032; A61M 5/14228;
(Continued)

(56) References Cited

U.S. PATENT DOCUMENTS 5,109,333 A    4/1992  Kubota
7,582,089 B2   9/2009  Schiebler
(Continued)

OTHER PUBLICATIONS

Kalpen et al., Acoustic Transmission of Biomedical Data via the Intercommunication System of an MRI, 3 pages (Year: 2018).*
Anonymous: "Coprocessor—Wikipedia", Sep. 20, 2015.

*Primary Examiner* — Thuy Dao

(57) ABSTRACT

The present disclosure relates to systems and methods for controlling an MRI safe patient care/monitoring system. The system may include a an MRI safe infusion pump that contains a co-processor which acts as a central brain for all other patient care/monitoring devices in the MRI room. The co-processor is separated from the primary processor by a buffer in the infusion pump's memory, so that no actions by the co-processor can affect the primary processor. The co-processor controls the display software, alert software and alerts database. All other patient care/monitoring devices are connected to the MRI safe infusion pump in a daisy chain, so that they can share a single connection to outside the MRI room. Outside the MRI room the co-processor has access to the remote control & display, which contains the remote control GUI, and to the internet, through which it will access an external medical network, which contains an algorithm database. The algorithm database has (Continued)

data processing algorithms for a variety of patient care/monitoring devices. allowing simpler "dumb" devices to be connected and still have "smart" functionality.

15 Claims, 7 Drawing Sheets

(51) Int. Cl.
  *A61M 5/172*  (2006.01)
  *A61B 5/00*  (2006.01)
  *A61M 5/168*  (2006.01)
  *G16H 40/67*  (2018.01)
  *G16H 40/20*  (2018.01)
  *G05B 19/042*  (2006.01)
  *H04L 29/08*  (2006.01)
  *G16Y 40/10*  (2020.01)
  *G16Y 40/30*  (2020.01)
  *G16Y 10/60*  (2020.01)

(52) U.S. Cl.
  CPC ....... *H04L 67/125* (2013.01); *A61M 2205/18* (2013.01); *A61M 2205/3553* (2013.01); *A61M 2205/3584* (2013.01); *A61M 2205/50* (2013.01); *A61M 2205/502* (2013.01); *A61M 2205/52* (2013.01); *G05B 2219/21039* (2013.01); *G16Y 10/60* (2020.01); *G16Y 40/10* (2020.01); *G16Y 40/30* (2020.01)

(58) Field of Classification Search
  CPC .... A61M 5/172; A61M 5/007; A61M 5/1413; A61M 2205/14; A61M 39/26; A61M 5/14546; A61N 1/3718; A61N 1/06; A61N 1/3754; A61N 1/05; G16H 40/67; G16H 40/20; G16H 40/10; G16H 20/17
  See application file for complete search history.

(56) References Cited

U.S. PATENT DOCUMENTS

| | | | |
|---|---|---|---|
| 8,718,747 B2 * | 5/2014 | Bjornerud | A61B 6/486 600/431 |
| 10,617,821 B2 * | 4/2020 | Susi | A61M 5/14228 |
| 2003/0058502 A1 | 3/2003 | Griffiths | |
| 2008/0171931 A1 | 7/2008 | Machke | |
| 2010/0031443 A1 | 2/2010 | Georgiev | |
| 2011/0009733 A1 | 1/2011 | Susi | |
| 2013/0172729 A1 | 7/2013 | Kocaturk | |
| 2013/0317753 A1 | 11/2013 | Kamen | |
| 2014/0100519 A1 | 4/2014 | Susi | |

* cited by examiner

SYSTEM AND METHOD FOR MONITORING PATIENT IN A MAGNETIC RESONANCE IMAGING ENVIRONMENT

CROSS REFERENCE TO RELATED APPLICATIONS

This application is the U.S. National Phase application under 35 U.S.C. § 371 of International Application No. PCT/EP2016/082943, filed Dec. 30 2016, published as WO 2017/114960 on Jul. 6, 2017, which claims the benefit of U.S. Provisional Patent Application No. 62/274,057 filed Dec. 31, 2015. These applications are hereby incorporated by reference herein.

BACKGROUND

The present disclosure relates generally to patient monitoring and patient care. More particularly, the present disclosure relates to a system and method useful in monitoring and caring for patients in a magnetic resonance imaging (MRI) room.

Smart electronic devices such as patient care and patient monitoring devices need expensive shielding to function properly in an MRI room, including properly transmitting data to outside of the MRI room. However, such expensive shielding can add cost to the overall medical expenses charged by the medical service providers providing patient care and patient monitoring using an MRI, as multiple patient care or patient monitoring devices are used to continuously monitor or treat patients in an MRI room.

SUMMARY OF THE CLAIMED INVENTION

In an exemplary embodiment, the MRI safe patient care/monitoring system comprises an MRI safe infusion pump that contains a co-processor which acts as a central brain for all other patient care/monitoring devices in the MRI room. The co-processor is separated from the primary processor by a buffer in the infusion pump's memory, so that no actions by the co-processor can effect the primary processor, and hence the infusion pump's, function in any way. The co-processor controls the display software, alert software and alerts database. All other patient care/monitoring devices are connected to the MRI safe infusion pump in a daisy chain, so that they can share a single connection to outside the MRI room. Outside the MRI room, the co-processor has access to the remote control & display, which contains the remote control GUI, and to the internet, through which it will access an external medical network that contains an algorithm database. The algorithm database has data processing algorithms for a variety of patient care/monitoring devices. This is for when a "dumb" device is part of the daisy chain, the display software will go out to the algorithm database and download the data processing algorithm and assume control of the dumb device. The display software begins when other patient care/monitoring device(s) are connected. It will first check to make sure all connected devices are MRI safe, and then which devices are "smart" enough to retain control of their function and which devices are "dumb" thereby needing the pump to assume control. The display software will then dynamically update the remote control GUI with the data feed from all connected devices. The alert software will then run, allowing the caregiver to import alert thresholds from other devices, such as the patient transfer device, or manually set the alert thresholds. These values, imported or caregiver defined, are placed in the alerts database.

In yet another exemplary embodiment, the MRI safe patient care/monitoring method includes: using a co-processor in a MRI safe infusion pump as a central brain for all other patient monitoring/care devices; connecting all other devices to the infusion pump in a daisy chain, which allows for all information from and control of those devices to be sent to an external controller in the MRI control room through a single communication channel; and the co-processor can also control additional devices that have less processing power, allowing for simpler "dumb" devices to be connected and still have "smart" functionality.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings.

DETAILED DESCRIPTION

Figure 1:
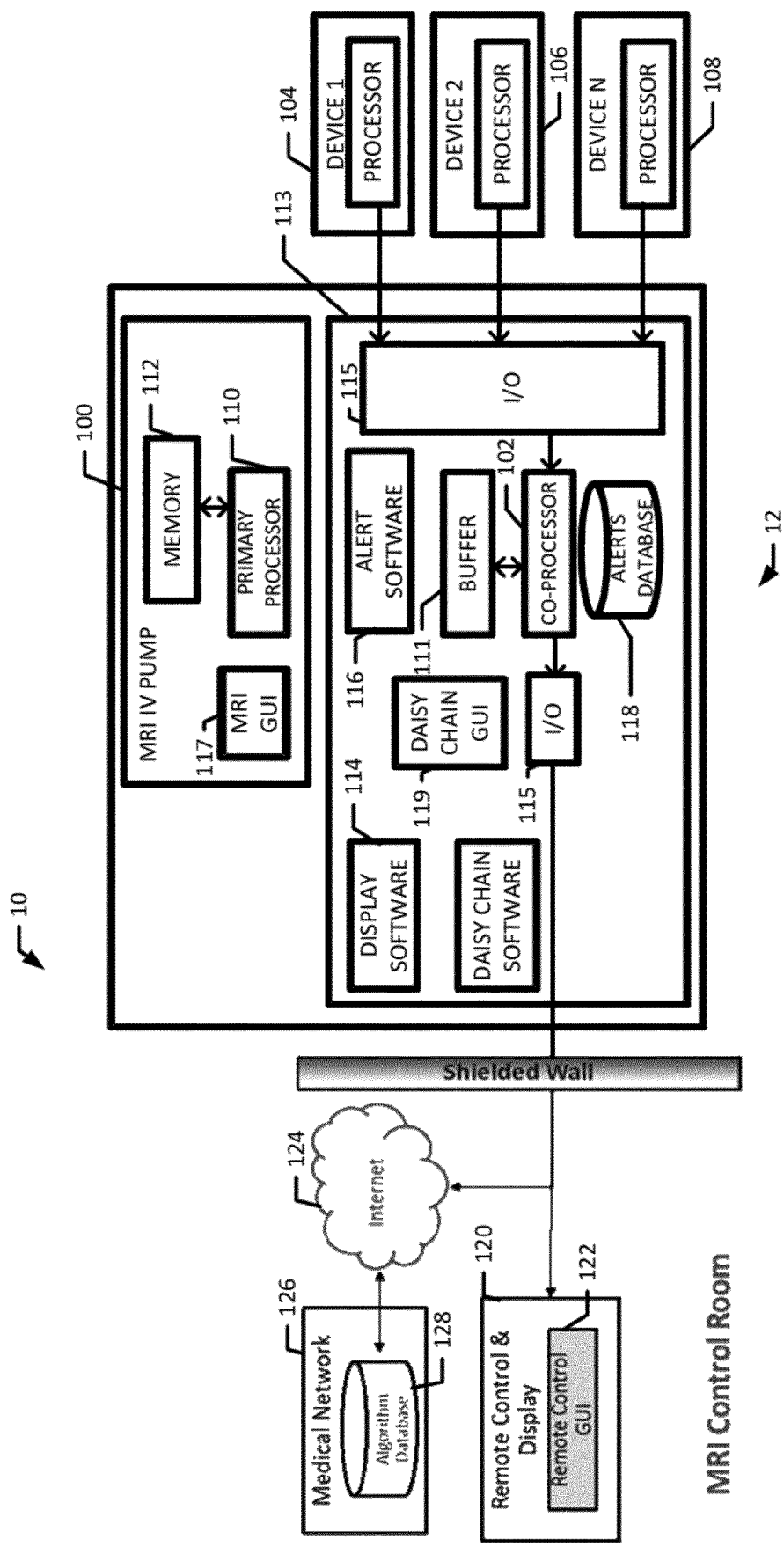
FIG. 1 shows a schematic diagram of an exemplary MRI safe patient care/monitoring system according to some embodiments of the present disclosure.

FIG. 1 shows the MRI safe patient monitoring/treatment system 10 according to an embodiment of the present disclosure. The system 10 includes an MRI safe infusion pump 100 that contains a co-processor 102 which acts as a central brain for all other patient care/monitoring devices 104-108 (e.g., ventilator, IV pump, etc.) in the MRI room 12. The co-processor 102 is separated from the primary processor 110 by a buffer 111 in the infusion pump's memory 112, so that no actions by the co-processor can affect the primary processor, and hence the infusion pump's, function in any way. In one embodiment, the daisy chain hardware 113 that includes but is not limited to the co-processor 102 and one or more I/O devices 115 are positioned within the MRI infusion pump 100. As shown, the daisy chain hardware 113 is physically and electrically isolated from primary processor 110. Thus, the primary processor 110 and memory 112 only operate the MRI pump 100; while the co-processor 102 and buffer 111 are limited to serving only the external devices 104-108 that are daisy chained. As such, these processors each have their associated own displays and GUIs 117 and 119.

The co-processor 102 controls the display software 114, alert software 116 and alerts database 118. All other patient care/monitoring devices 104-108 are connected to the MRI safe infusion pump 100 in a daisy chain, so that they can share a single connection to outside the MRI room 12. Outside the MRI room 12, the co-processor 102 has access to the remote control and display 120, which contains the remote control GUI 122, and to the Internet 124 or other network, through which it will access an external medical network 126 that contains an algorithm database 128. The algorithm database 128 has data processing algorithms for a variety of patient care/monitoring devices 104-108. The data processing algorithms can be used when a "dumb" device is part of the daisy chain. The display software 114 will enable the co-processor 102 to access the algorithm database 128, download the data processing algorithm, and assume control of the dumb device. The display software 114 begins when other patient care/monitoring device(s) are connected. It will first enable the system to verify and confirm that all connected devices 104-108 are MRI safe, and then which devices are "smart" enough to retain control of their function and which devices are "dumb" and thus need the pump to assume control. The display software 114 will then dynamically update the remote control GUI 122 with the data feed from all connected devices 104-108. The alert software 116 will then execute, allowing a user (e.g., a doctor, nurse, caregiver, and other medical professionals) to import alert thresholds from other devices, such as the patient transfer device, or manually set the alert thresholds. These values, imported or user defined, are placed in the alerts database 118.

Figure 2:
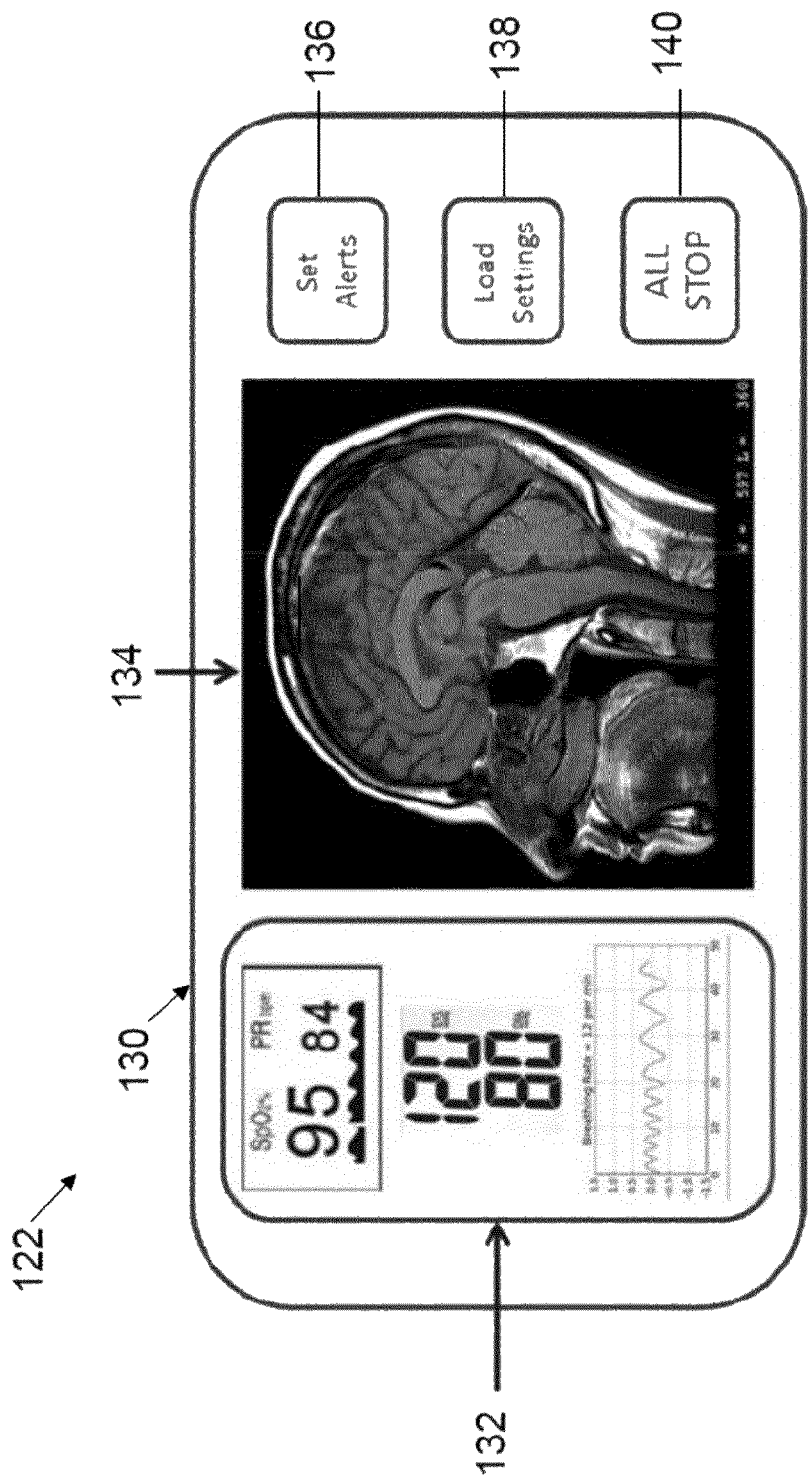
FIG. 2 shows a main screen of the remote control GUI according to an embodiment of the present disclosure.

FIG. 2 represents a main screen 130 of the graphical user interface 122 (GUI) for the remote control of the system according to some embodiments of the present disclosure. The remote control GUI 122 (main screen) has five fields: a sensor data feed display 132, a display of the MRI image data 134, a set alerts button 136, a load settings button 138 and an all stop button 140. The sensor data field 132 is populated by the display software 114. The MRI image field 134 is populated with image data from the MRI. The all stop button 140 provides an emergency shutdown of the MRI. The set alerts and load settings buttons 136 and 138, respectively, are controlled by the alert software 116. The load settings button 138 is highlighted when alert thresholds are available from the existing patient care/monitor devices 104-108. When the user selects load settings button 138, the alert thresholds are imported into the alert database 118. The set alerts button 136 opens the alerts setting screen 138 of the remote control GUI 122.

Figure 3:
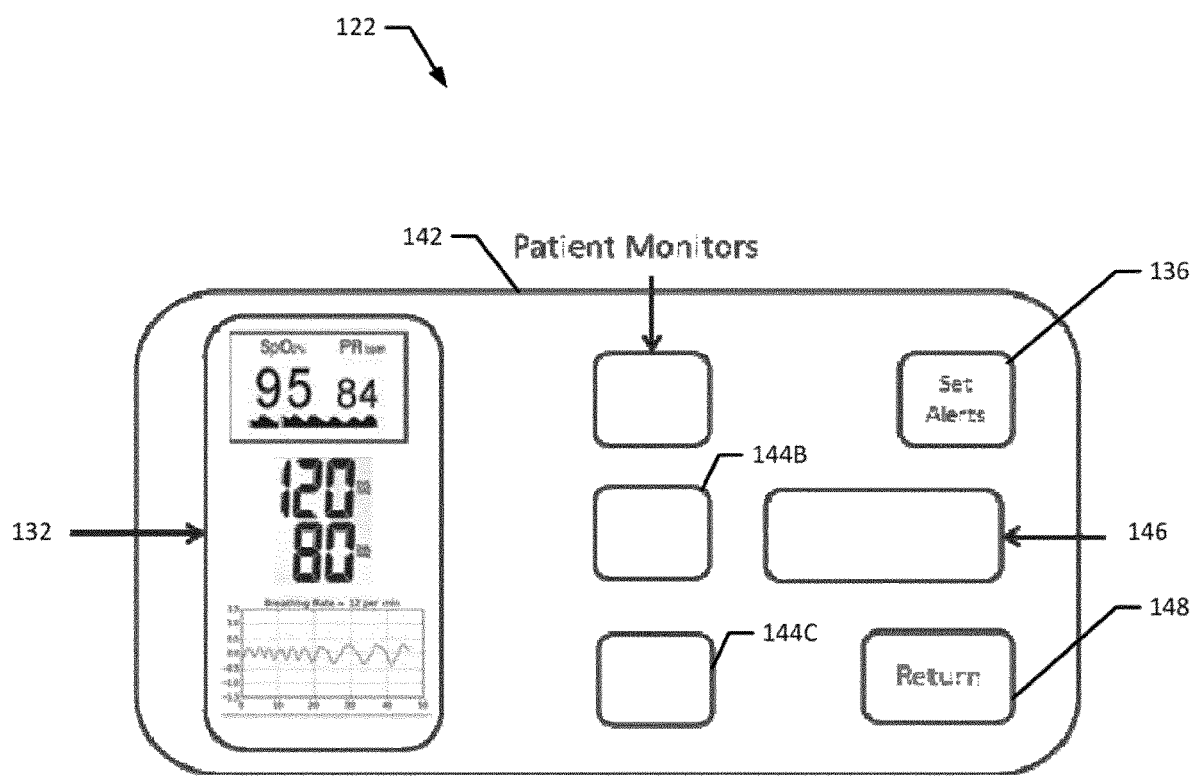
FIG. 3 shows an alert setting screen of the remote control GUI according to an embodiment of the disclosure.

FIG. 3 shows the alert setting screen 142 that is presented in the remote control GUI 122 when the user selects the "set alerts" button in the remote control GUI's main screen 130. The alert setting screen GUI 142 has five sections: a sensor data display 132 that is identical to that found in the remote control GUI's main screen 130, a series of radio buttons 144A-C next to each sensor data feed (in this figure labeled "Patient Monitors"), a "set alerts" button 136, an "alert threshold" box 146, and a "return" button 148. The user will select the radio button 144A-C next to the sensor data feed 136 for which they wish to set an alert threshold. This will give the user access to the "alert threshold" box 146, which is a free form box that enables the user to set an alert threshold for that patient monitor. That threshold is not entered into the alert database 118 until the user hits the "set alerts" button 136. The user can keep adjusting or setting new alert thresholds until they select the "return" button 148, which will bring them back to the remote control GUI's main screen 130.

Figure 4:
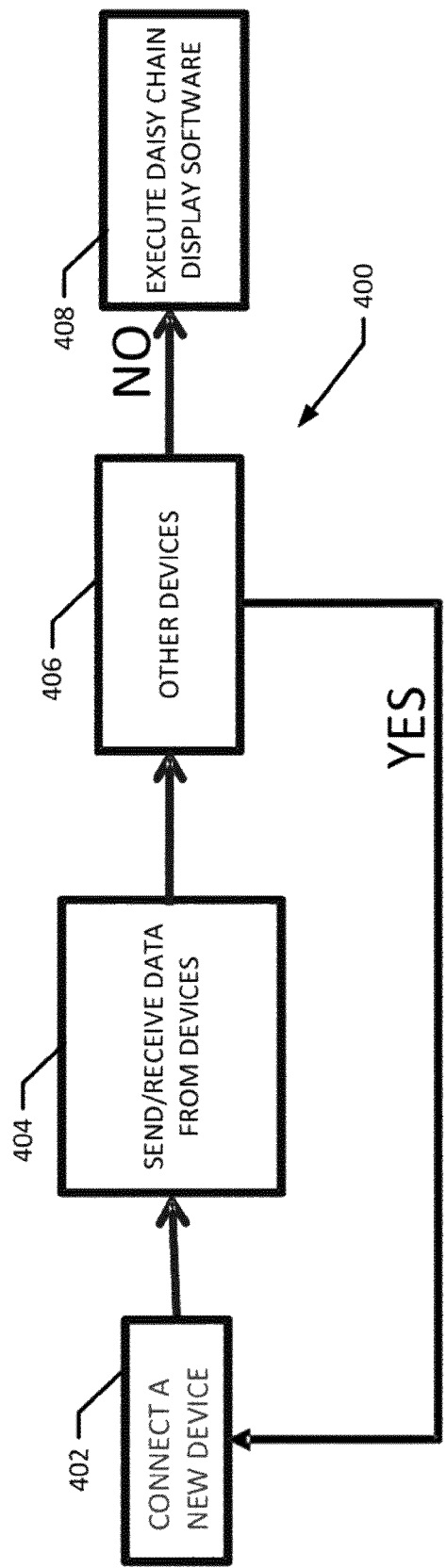
FIG. 4 shows a flowchart of the daisy chain software according to a preferred embodiment of the disclosure.

FIG. 4 shows a flowchart of a method 400 performed or caused to be performed by an instance of the daisy chain software 121 executing at the co-processor 102 according to a preferred embodiment of the disclosure. In one embodiment, the co-processor 102 executing the daisy chain software 121 polls for new patient care/monitoring devices and connects to them if found at step 402. Data is then transferred back and forth among the patient care/monitoring devices 104-108 and the medical network 126, at step 404, via a communications link such as the Internet 124 without burdening the computing resources of the main (primary) processor. A query is initiated at step 406 to determine if there is at least one other new device connected to the chain of devices. If there is at least one new device, the method 400 returns to step 402 where the new device is brought into communication with the co-processor 102. If no new devices are identified at step 406, then the co-processor executes the daisy chain display software 114 at step 408.

Figure 5:
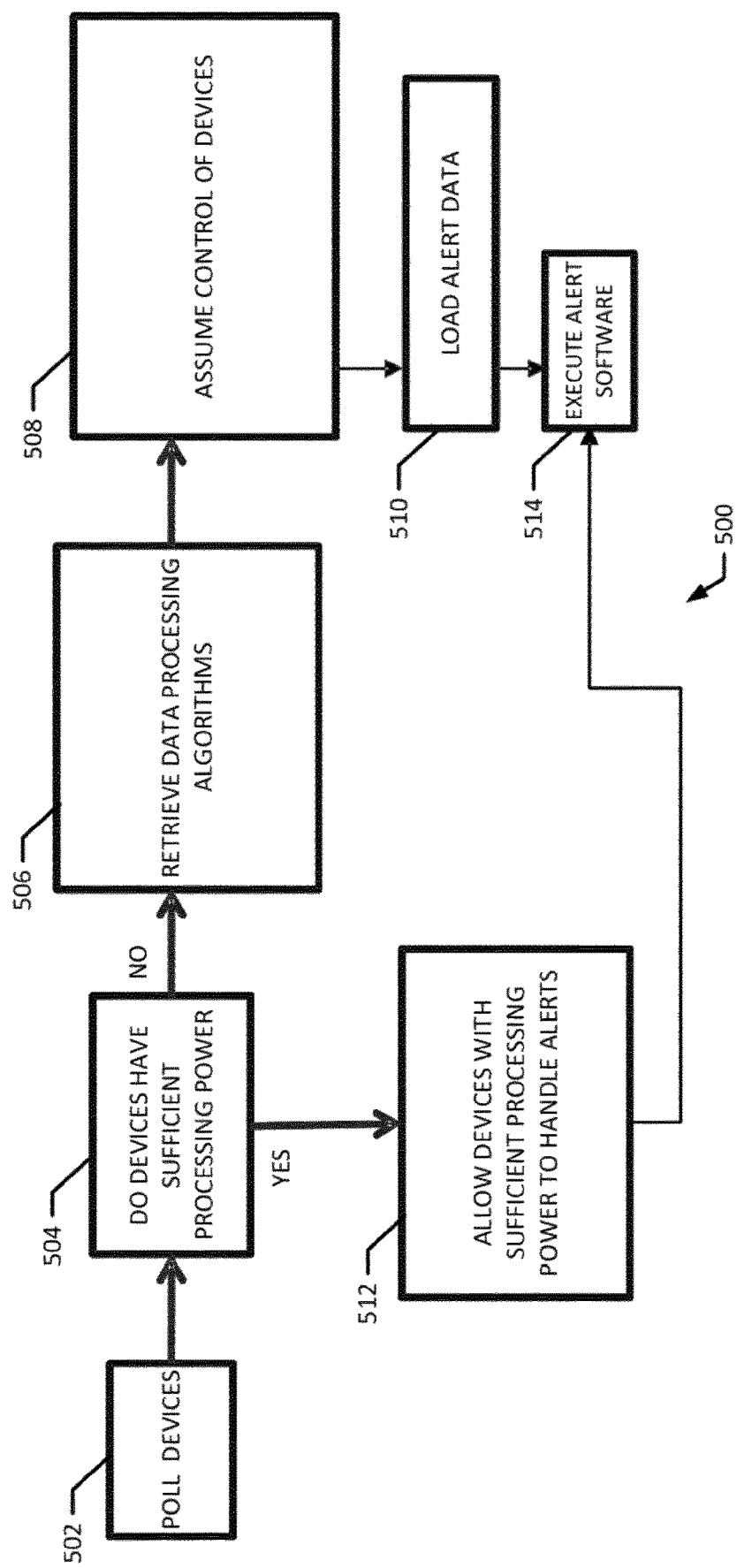
FIG. 5 shows a flowchart of the display software according to a preferred embodiment of the disclosure.

FIG. 5 shows a flowchart of the of a method 500 performed or caused to be performed by an instance of the daisy chain display software 114 executing at the co-processor 102 according to a preferred embodiment of the disclosure. The co-processor 102 executing display software 114 polls the connected devices 104-108 at step 502 are polled to determine if they are MRI safe. In one embodiment, if any of the patient monitoring/care device(s) 104-108 are not MRI safe, then the MRI is disabled, the "all stop" button 140 on the remote control GUI 122 will flash and the program will end. If all of the device(s) are MRI safe, then the devices 104-108 are queried for their processor specifications at step 504. If all connected devices 104-108 have a sufficient level of processing power, they are allowed to control their own functions at step 506, and their data feeds are displayed in the sensor data field of the remote control GUI 122. In various aspects, the threshold for sufficient processing power is determined by a manufacturer preset value or a user defined value. If any connected device(s) fall below the acceptable threshold for processing power at step 504, then the appropriate data processing algorithm is retrieved by the co-processor 102 from the algorithm database 128 on the external medical network 126 and stored in the buffer 111 at step 506. Full or at least partial control of the device(s) having insufficient processing power is then assumed by the co-processor 102 at step 508. In one aspect, the co-processor 102 not only passes device data thru to the display but it also actively manages any alerts for the device at step 510. Furthermore, the remote control GUI 122 is adjusted to display the patient monitoring device feed in the sensor data field of the remote control GUI 122. Thus, all relevant information from the patient care/monitoring device can be displayed on the remote control GUI 122. The alert software 116 is then prompted at step 514. As shown, the devices 104-108 that have sufficient processing power at step 512 may also execute an instance of the alert software at step 514.

In various aspects, either the devices 104-108 control their function and transmit their data feed alerts to the daisy chain display GUI 119 directly where the co-processor 102 just assists in passing thru device data. Alternately, the co-processor 102 passes thru device data but also loads the algorithms from the external medical network and uses the algorithms to drive the alerts. In one embodiment, both the device data and the alerts from the alerts database are used to drive the display on the daisy chain GUI 119. In another embodiment, a separate display is used to continually show the MRI GUI.

Figure 6:
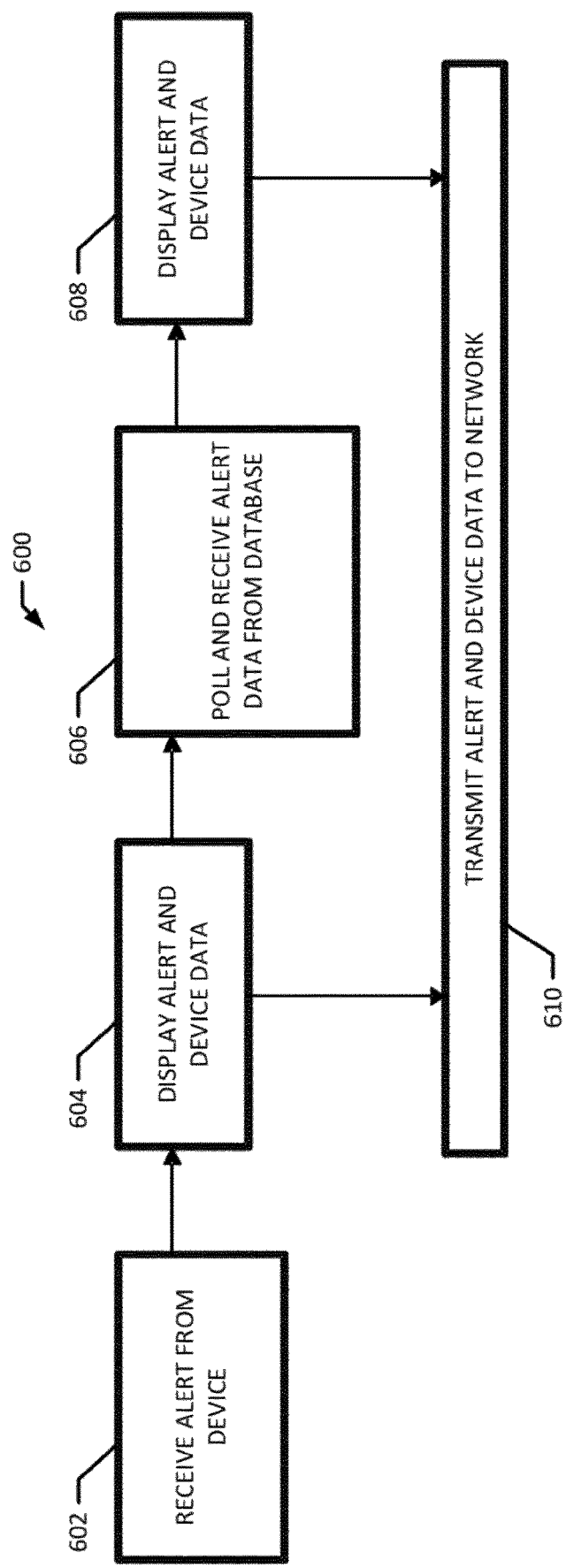
FIG. 6 shows a flowchart of the alert software according to a preferred embodiment of the disclosure.

FIG. 6 shows a flowchart of a method 600 performed or caused to be performed by an instance of the alert software 116 executing at the co-processor 102 or a processor of the devices 104-108 having sufficient processing power according to a preferred embodiment of the disclosure. In various embodiments, the alert software 116 is executed at the co-processor 102 to send device data and alerts to the daisy chain GUI 119 for both the devices that can control their functions directly or for devices that cannot control their functions directly.

At step 602, the co-processor 102 executing the alert software 116 receives alert from the devices 104-108 that the co-processor controls. At step 604, the co-processor 102 displays device data and alerts on daisy chain GUI 119 and sends the alerts to the medical network at step 610. Alternately, the co-processor 102 polls and receives alert data from the alert database for the devices 104-108 that cannot control their own alerts at step 606. At step 608, the co-processor 102 displays device data and alerts on the daisy chain GUI 119 for those devices that control their own alerts. The co-processor 102 also sends the alerts to the medical network at step 610.

Figure 7:
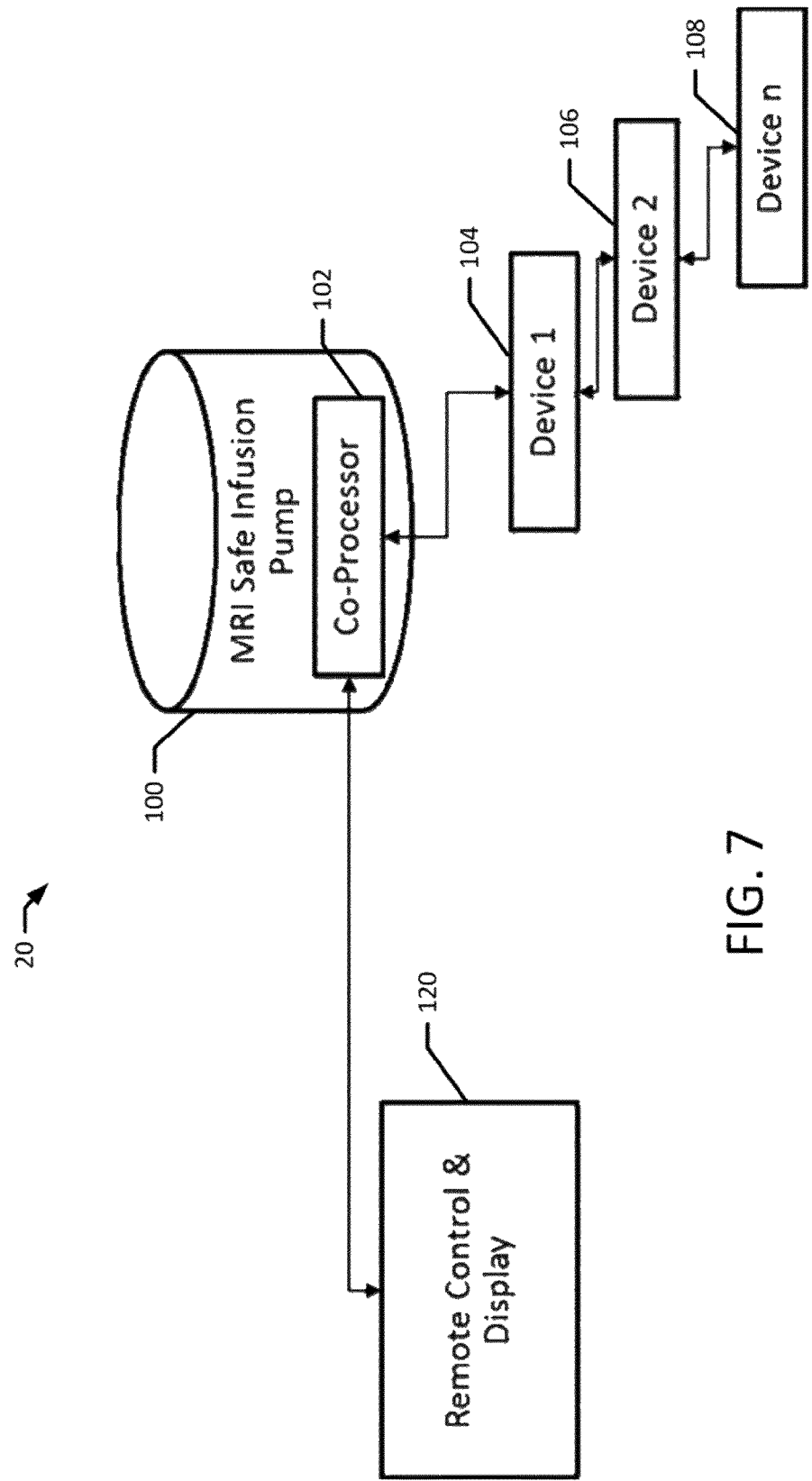
FIG. 7 shows a schematic diagram of another exemplary system according to some embodiments of the disclosure.

FIG. 7 shows a schematic diagram of another exemplary system 20 according to some embodiments of the disclosure. The intelligence is removed from peripheral devices 104-108 (e.g., patient monitor, ventilator, IV pump) in an MRI room, and a central processor 102 is used to both calculate values for those devices and relaying that information to a remote control 120, whose display is dynamically updated based upon the devices connected to the central processor 102.

By connecting all patient care/monitoring devices 104-108 to the infusion pump 100 in a daisy chain, the system of the present disclosure allows for all information from, and control of, those devices to be sent to an external controller in the MRI control room through a single communication link/channel. The co-processor 102 can also control additional devices that have less processing power, allowing simpler "dumb" devices to be connected and still have "smart" functionality.

The present invention is not intended to be restricted to the several exemplary embodiments of the invention described above. Other variations that may be envisioned by those skilled in the art are intended to fall within the disclosure.

The invention claimed is:

1. An MRI safe patient care/monitoring system comprising:
   a co-processor in a MRI safe infusion pump that acts as a central brain for all patient monitoring/care devices, the co-processer being disposed in a daisy chain system; wherein the daisy chain system is disposed with in a housing of the infusion pump and includes memory including a buffer;
   at least one alert database storing alert data for the patient care/monitoring devices;
   an input/output device; and
   a display device;
   the patient care/monitoring devices being connected to the infusion pump in a daisy chain, which allows for all information from and control of those devices to be sent to an external controller in the MRI control room through a single communication channel;
   wherein the co-processor can also control additional devices that have less processing power, allowing simpler "dumb" devices to be connected and still have "smart" functionality.

2. The system of claim 1, where the infusion pump further comprises a primary processor and where the primary processor is electrically isolated from the co-processor.

3. The system of claim 1, wherein the co-processor is isolated from the primary processor by at least one buffer.

4. The system of claim 1, further comprising:
   memory; and
   at least one algorithm database storing data processing algorithms for the patient care/monitoring devices; and
   at least one alert database storing alert data for the patient care/monitoring devices.

5. The system of claim 1, wherein the infusion pump and the patient care/monitoring devices are controlled from a remote location.

6. A system for monitoring and controlling one or more devices in an MRI environment, the system comprising:
   an infusion pump, the infusion pump comprising a pump processor, a pump memory, and a pump display;
   a patient monitoring device, the monitoring device including a device processor and the monitoring device in communication with a co-processor; and
   a daisy chain controller, the daisy chain controller comprising the co-processor, memory including a buffer, a daisy chain display, and an alert database; the co-processor to:
   poll the system for initiating communication with the patient monitoring device;
   transmit device data from the patient monitoring device to a medical network;
   determine if there is another patient monitoring device in communication with the patient monitoring device; and
   initiate communication with the other patient monitoring device, if present.

7. The system of 6, further comprising the co-processor to:
   poll the patient monitoring device to determine if the monitoring device is MRI safe;
   query the patient monitoring device for the specifications of the device processor;
   retrieve a data processing algorithm for the patient monitoring device;
   store the data processing algorithm in the buffer;
   pass device data from the patient monitoring device to the pump display; and
   manage an alert for the patient monitoring device.

8. The system of 7, further comprising the co-processor to:
   display device data and the alert at the daisy chain display; and
   transmit the alert to a medical network.

9. The system of 6, further comprising the co-processor to:
   poll the patient monitoring device for an alert;
   receive alert data from the patient monitoring device;
   display device data and the alert data at the daisy chain display; and
   transmit the alert data to a medical network.

10. The system of 6, wherein the co-processor is in communication with the medical network via a local area network or the internet.

11. The system of 6, wherein the daisy chain controller is disposed within a housing of the infusion pump.

12. The system of claim 6, wherein the co-processor is electrically isolated from the pump processor.

13. A method for monitoring and controlling one or more devices in an MRI environment, wherein the MRI environment includes the system of claim 1 the method comprising:
   polling the system for initiating communication with the patient monitoring device;
   transmitting device data from the patient monitoring device to a medical network;

determining if there is another patient monitoring device in communication with the patient monitoring device; and initiating communication with the other patient monitoring device, if present.

14. The method of 13, further comprising:

polling the patient monitoring device to determine if the monitoring device is MRI safe;

querying the patient monitoring device for the specifications of the device processor;

retrieving a data processing algorithm for the patient monitoring device;

storing the data processing algorithm in the buffer;

passing device data from the patient monitoring device to the pump display;

managing an alert for the patient monitoring device displaying device data and the alert at the daisy chain display; and transmitting the alert to a medical network.

15. The method of 13, further comprising:

polling the patient monitoring device for an alert;

receiving alert data from the patient monitoring device;

displaying device data and the alert data at the daisy chain display; and transmitting the alert data to a medical network.

* * * * *